(12) United States Patent
Gillespie et al.

(10) Patent No.: US 7,098,333 B2
(45) Date of Patent: Aug. 29, 2006

(54) PYRROLO[2,3-D]PYRIMIDINE AND THEIR USE AS PURINERGIC RECEPTOR ANTAGONISTS

(75) Inventors: Roger John Gillespie, Wokingham (GB); Joanne Lerpiniere, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 81 days.

(21) Appl. No.: 10/250,940

(22) PCT Filed: Jan. 10, 2002

(86) PCT No.: PCT/GB02/00095

§ 371 (c)(1),
(2), (4) Date: Nov. 13, 2003

(87) PCT Pub. No.: WO02/055084

PCT Pub. Date: Jul. 18, 2002

(65) Prior Publication Data

US 2004/0092537 A1    May 13, 2004

(30) Foreign Application Priority Data

Jan. 10, 2001 (GB) ................. 0100622.0

(51) Int. Cl.
*C07D 487/04* (2006.01)
(52) U.S. Cl. ............................................. 544/280
(58) Field of Classification Search .......... 544/280; 514/265.1
See application file for complete search history.

(56) References Cited

FOREIGN PATENT DOCUMENTS

| EP | 0 496 617 A1 | 7/1992 |
|---|---|---|
| JP | 07010876 A2 * | 1/1995 |
| WO | WO 93/20078 A1 | 10/1993 |
| WO | WO 94/13676 A1 | 6/1994 |
| WO | WO 94/17803 A1 | 8/1994 |
| WO | WO 00/61586 A1 | 10/2000 |

OTHER PUBLICATIONS

LeWitt, Peter A., Pharmacotherapy, 20, pp. 26S-32S, 2000.*
Joergensen, Anker; Girgis, Nabih S.; Pedersen, Erik B., Liebigs Annalen der Chemie (1), 142-8 (English) 1985.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Kulisevsky, Jaime; Barbanoj, Manel; Gironell, Alexandre; Antonijoan, Rosa; Casas, Miquel; Pascual-Sedano, Berta, Clinical Neuropharmacology. 25(1):25-31, Jan./Feb. 2002, abstract only.*
Morelli, Micaela, Experimental Neurology, 184, 20-23, 2003.*
Tuite, Paul et al, Expert. Opin. Investig. Drugs, 12, 1335-1352, 2003.*
Bibbiani, F. et al, Experimental Neurology, 184, 285-194, 2003.*
Spiros Konitsiotis, Expert. Opin. Investig. Drugs, 14, 377-392 2005.*
Anonymous, Drug and Therapeutic Bulletin, 35, pp. 36-40, 1999.*
Chemical Abstracts, vol. 118, No. 3, Jan. 18, 1993, Columbus, Ohio, US; abstract No. 22077, Suzuki, Hitomi et al: "Sodium telluride in N-methyl-2-pyrrolidone. Reduction of aromatic carbronyl compounds to alcohols and formation of pyrrolo[2,3-d]pyrimidines (7-deaza-9H-purines) from aromatic nitriles," XP002197327, RN:144587-22-4, 144587-23-5, 144587-24-6, abstract & J. Org. Chem. (1993), 58(1), 241-4.
Chemical Abstracts, vol. 121, No. 9, Aug. 29, 1994, Columbus, Ohio, US; abstract No. 108677, Bouillon, Jean Philippe et al.: "Trifluoromethylated pyrimidines starting from.beta.-trifluoroacetyl-lactams,-lactone and -cyclanone," XP002197328, RN: 156870-48-3, abstract, & HETEROCYCLES (1994), 37(2), 915-32.

* cited by examiner

*Primary Examiner*—Thomas C. McKenzie
(74) *Attorney, Agent, or Firm*—Foley & Lardner LLP

(57) ABSTRACT

Use of a compound of the formula (I) wherein $R_1$ is selected from alkyl, alkoxy, aryloxy, alkylthio, arylthio, aryl, halogen, CN, $NR_7R_8$, $NR_6COR_7$, $NR_6CO_2R_9$ and $NR_6SO_2R_9$; $R_2$ is selected from aryl attached via an unsaturated carbon; $R_3$ and $R_4$ are independently selected from H, alkyl, halogen, alkoxy, alkylthio, CN and $NR_7R_8$; $R_5$ is selected from H, acyclic alkyl, $COR_6$, $CONR_7R_8$, $CONR_6NR_7R_8$, $CO_2R_9$ and $SO_2R_9$; $R_6$, $R_7$ and $R_8$ are independently selected from H, alkyl and aryl or where $R_7$ and $R_8$ are in an $NR_7R_8$ group $R_7$ and $R_8$ may be linked to form a hererocyclic group, or where $R_6$, $R_7$ and $R_8$ are in a ($CONR_6NR_7R_8$) group, $R_6$ and $R_7$ may be linked to form a hererocyclic group; and $R_9$ is selected from alkyl and aryl, or a pharmaceutically acceptable salt thereof or prodrug thereof, in the manufacture of a medicament for the treatment or prevention of a disorder in which the blocking of purine receptors, particularly adenosine receptors and more particularly $A_{2A}$ receptors, may be beneficial, particularly wherein said disorder is a movement disorder such as Parkinson's disease or said disorder is depression, cognitive or memory impairment, acute or chronic pain, ADHD or narcolepsy, or for neuroprotection in a subject; compounds of formula (I) for use in therapy; and novel compounds of formula (I) per se

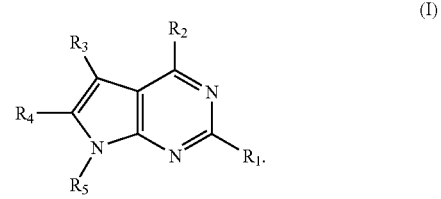

(I)

37 Claims, No Drawings

PYRROLO[2,3-D]PYRIMIDINE AND THEIR USE AS PURINERGIC RECEPTOR ANTAGONISTS

The present invention relates to pyrrolo[2,3-d]pyrimidin derivatives and their use in therapy. In particular, the present invention relates to the treatment of disorders in which the reduction of purinergic neurotransmission could be beneficial. The invention relates in particular to blockade of adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. et al., *Trends Pharmacol. Sci.* 1997, 18, 338–344) and in the treatment of cerebral ischaemia (Gao, Y. and Phillis, J. W., *Life Sci.* 1994, 55, 61–65). The potential utility of adenosine $A_{2A}$ receptor antagonists in the treatment of movement disorders such as Parkinson's Disease has recently been reviewed (Mally, J. and Stone, T. W., *CNS Drugs,* 1998, 10, 311–320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407–422). This therapeutic potential has resulted in considerable recent research endeavour within the field of adenosine receptor agonists and antagonists (Bhagwhat, S. S.; Williams, M. *Exp. Opin. Ther. Patents* 1995, 5,547–558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143–156). The adenosine receptors are present in the CNS (Fredholm, B. B., *News Physiol. Sci.,* 1995, 10, 122–128).

The design of $P_1$ receptor-mediated agents has been reviewed (Jacobson, K. A., Suzuki, F., *Drug Dev. Res.,* 1997, 39, 289–300; Baraldi, P. G. et al., *Curr. Med. Chem.* 1995, 2, 707–722), and such compounds are claimed to be useful in the treatment of cerebral ischemia or neurodegenerative disorders, such as Parkinson's disease (Williams, M. and Burnstock, G. *Purinergic Approaches Exp. Ther.* (1997), 3–26. Editor: Jacobson, Kenneth A.; Jarvis, Michael F. Publisher: Wiley-Liss, New York, N.Y.)

It has been speculated that xanthine derivatives such as caffeine may offer a form of treatment for attention-deficit hyperactivity disorder (ADHD). A number of studies have demonstrated a beneficial effect of caffeine on controlling the symptoms of ADHD (Garfinkel, B. D. et al., *Psychiatry,* 1981, 26, 395–401). Antagonism of adenosine receptors is thought to account for the majority of the behavioural effects of caffeine in humans and thus blockade of adenosine $A_{2A}$ receptors may account for the observed effects of caffeine in ADHD patients. Therefore a selective $A_{2A}$ receptor antagonist may provide an effective treatment for ADHD but without the unwanted side-effects associated with current therapy.

Adenosine receptors have been recognised to play an important role in regulation of sleep patterns, and indeed adenosine antagonists such as caffeine exert potent stimulant effects and can be used to prolong wakefulness (Porkka-Heiskanen, T. et al., *Science,* 1997, 276, 1265–1268). Recent evidence suggests that a substantial part of the actions of adenosine in regulating sleep is mediated through the adenosine $A_{2A}$ receptor (Satoh, S., et al., *Proc. Natl. Acad. Sci.,* USA, 1996). Thus, a selective $A_{2A}$ receptor antagonist may be of benefit in counteracting excessive sleepiness in sleep disorders such as hypersomnia or narcolepsy.

It has recently been observed that patients with major depression demonstrate a blunted response to adenosine agonist-induced stimulation in platelets, suggesting that a dysregulation of $A_{2A}$ receptor function may occur during depression (Berk, M. et al, 2001, *Eur. Neuropsychophannacol.* 11, 183–186). Experimental evidence in animal models has shown that blockade of $A_{2A}$ receptor function confers antidepressant activity (El Yacoubi, M et al. *Br. J. Pharmacol.* 2001, 134, 68–77). Thus, $A_{2A}$ receptor antagonists may offer a novel therapy for the treatment of major depression and other affective disorders in patients.

The pharmacology of adenosine $A_{2A}$ receptors has been reviewed (Ongini, E.; Fredholm, B. B. *Trends Pharmacol. Sci.* 1996, 17(10), 364–372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Natl. Acad. Sci.*

U.S.A. 1991, 88, 7238–41) have been summarised in two more recent articles (Fuxe, K. et al., *Adenosine Adenine Nucleotides Mol. Biol. Integr. Physiol.*, [Proc. Int. Symp.], 5th (1995), 499–507. Editors: Belardinelli, Luiz; Pelleg, Amir. Publisher: Kluwer, Boston, Mass.; Ferre, S. et al., *Trends Neurosci.* 1997, 20, 482–487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 162–4; Mandhane, S. N. et al., *Eur. J. Pharmacol.* 1997, 328, 135–141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder may also be treated. The neuroprotective effect of adenosine $A_{2A}$ antagonists has been reviewed (Ongini, E.; Adami, M.; Ferri, C.; Bertorelli, R., *Ann. N. Y. Acad. Sci.* 1997, 825(Neuroprotective Agents), 30–48). In particular, compelling recent evidence suggests that blockade of $A_{2A}$ receptor function confers neuroprotection against MPTP-induced neurotoxicity in mice (Chen, J-F., *J. Neurosci.* 2001, 21, RC143). In addition, several recent studies have shown that consumption of dietary caffeine, a known adenosine $A_{2A}$ receptor antagonist, is associated with a reduced risk of Parkinson's disease in man (Ascherio, A. et al, *Ann Neurol.*, 2001, 50, 56–63; Ross G W, et al., *JAMA*, 2000, 283, 2674–9). Thus, $A_{2A}$ receptor antagonists may offer a novel treatment for conferring neuroprotection in neurodegenerative diseases such as Parkinson's disease.

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett.*, 1993, 323, 141–144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994, 46, 515–517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263–268). The structure activity relationship (SAR) of KF 17837 has been published (Shimada, J. et al., *Bioorg. Med. Chem. Lett.* 1997, 7, 2349–2352). Recent data has also been provided on the $A_{2A}$ receptor antagonist KW-6002 (Kuwana, Y et al., *Soc. Neurosci. Abstr.* 1997, 23, 119.14; and Kanda, T. et al., *Ann. Neurol.* 1998, 43(4), 507–513).

New non-xanthine structures sharing these pharmacological properties include SCH 58261 and its derivatives (Baraldi, P. G. et al., Pyrazolo[4,3-e]-1,2,4-triazolo[1,5-c]pyriridine Derivatives: Potent and Selective $A_{2A}$ Adenosine Antagonists. *J. Med. Chem.* 1996, 39, 1164–71). SCH 58261 (7-(2-phenylethyl)-5-amino-2-(2-furyl)-pyrazolo-[4,3-e]-1,2,4-triazolo[1,5-c] pyrimidine) is reported as effective in the treatment of movement disorders (Ongini, E. *Drug Dev. Res.* 1997, 42(2), 63–70) and has been followed up by a later series of compounds (Baraldi, P. G. et al., *J. Med. Chem.* 1998, 41(12), 2126–2133).

The foregoing discussion indicates that a potentially effective treatment for movement disorders in humans would comprise agents which act as antagonists at adenosine $A_{2A}$ receptors.

It has now been found that pyrrolo[2,3-d]pyrimidine derivatives, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be useful for the treatment of disorders in which the blocking of purine receptors, particularly adenosine receptors and more particularly adenosine $A_{2A}$ receptors, may be beneficial. In particular such compounds may be suitable for the treatment of movement disorders, such as disorders of the basal ganglia which result in dyskinesias. Disorders of particular interest in the present invention include Parkinson's disease, Alzheimer's disease, spasticity, Huntington's chorea and Wilson's disease.

Such compounds may also be particularly suitable for the treatment of depression, cognitive or memory impairment including Alzheimer's disease, acute or chronic pain, ADHD, narcolepsy or for neuroprotection.

According to the present invention there is provided the use of a compound of formula (I):

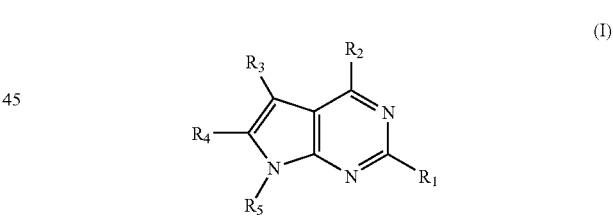

wherein $R_1$ is selected from alkyl, alkoxy, aryloxy, alkylthio, arylthio, aryl, halogen, CN, $NR_7R_8$, $NR_6COR_7$, $NR_6CONR_7R_8$, $NR_6CO_2R_9$ and $NR_6SO_2R_9$;

$R_2$ is selected from aryl attached via an unsaturated carbon;

$R_3$ and $R_4$ are independently selected from H, alkyl, halogen, alkoxy, alkylthio, CN and $NR_7R_8$;

$R_5$ is selected from H, acyclic alkyl, $COR_6$, $CONR_7R_8$, $CONR_6NR_7R_8$, $CO_2R_9$ and $SO_2R_9$;

$R_6$, $R_7$ and $R_8$ are independently selected from H, alkyl and aryl or where $R_7$ and $R_8$ are in an $NR_7R_8$ group, $R_7$ and $R_8$ may be linked to form a heterocyclic group, or where $R_6$, $R_7$ and $R_8$ are in a ($CONR_6NR_7R_8$) group, $R_6$ and $R_7$ may be linked to form a heterocyclic group; and $R_9$ is selected from alkyl and aryl, or a pharmaceutically acceptable salt or prodrug thereof, in the manufacture of a medicament for the treatment or prevention of a disorder in which the blocking of purine receptors, particularly adenosine receptors and more particularly $A_{2A}$ receptors, may be beneficial.

As used herein the term "alkyl", unless otherwise stated, means a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein, unless otherwise stated, includes alkyl (branched or unbranched), alkenyl (branched or unbranched), alkynyl (branched or unbranched), cycloalkyl, cycloalkenyl and cycloalkynyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl (preferably phenyl), or a heteroaromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl or indazolyl.

As used herein, the term "heteroaryl" means an aromatic group containing one or more heteroatom(s) preferably selected from N, O and S, such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl, pyrimidinyl, indolyl, pyrazinyl or indazolyl.

As used herein, the term "non-aromatic heterocyclyl" means a non-aromatic cyclic group containing one or more heteroatom(s) preferably selected from N, O and S, such as a cyclic amino group (including aziridinyl, azetidinyl, pyrrolidinyl, piperidyl, piperazinyl, morpholinyl) or a cyclic ether (including tetrahydrofuranyl).

As used herein, the term "alkoxy" means alkyl-O—. As used herein, the term "aryloxy" means aryl-O—.

As used herein, the term "halogen" means a fluorine, chlorine, bromine or iodine radical.

As used herein, the term "ortho,ortho-disubstituted aryl groups" refers to aryl groups which are substituted in both ortho positions of the aryl group relative to the point of attachment of the aryl group to the pyrimidine ring.

As used herein, the term "prodrug" means any pharmaceutically acceptable prodrug of a compound of the present invention.

Where any of $R_1$ to $R_{15}$ is selected from alkyl, alkoxy and thioalkyl, in accordance with formula (I) as defined above, then that alkyl group, or the alkyl group of the alkoxy or thioalkyl group, may be substituted or unsubstituted. Where any of $R_1$ to $R_{15}$ are selected from aryl, aryloxy and thioaryl, in accordance with formula (I) as defined above, then said aryl group, or the aryl group of the aryloxy or thioaryl group, may be substituted or unsubstituted. Where $R_7$ and $R_8$, or $R_6$ and $R_7$, are linked to form a heterocyclic group, the heterocyclic group may be substituted or unsubstituted. Where substituted, there will generally be 1 to 3 substituents present, preferably 1 substituent. Substituents may include:

| Carbon-containing groups such as | |
|---|---|
| alkyl, aryl, arylalkyl; | (e.g. substituted and unsubstituted phenyl (including (alkyl)phenyl, (alkoxy)phenyl, (alkyl- and aryl-sulfonylamino)phenyl and halophenyl), (e.g. substituted and unsubstituted benzyl); |
| halogen atoms and halogen containing groups such as | |
| haloalkyl haloaryl | (e.g. trifluoromethyl), (e.g. chlorophenyl); |
| oxygen containing groups such as | |
| alcohols | (e.g. hydroxy, hydroxyalkyl, hydroxyaryl, (aryl)(hydroxy)alkyl), |
| ethers | (e.g. alkoxy, aryloxy, alkoxyalkyl, aryloxyalkyl, alkoxyaryl, aryloxyaryl), |
| aldehydes | (e.g. carboxaldehyde), |
| ketones | (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl), |
| acids | (e.g. carboxy, carboxyalkyl, carboxyaryl), |
| acid derivatives such as esters | (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl), |
| amides | (e.g. aminocarbonyl, mono- or di-alkylaminocarbonyl, cyclicaminocarbonyl, aminocarbonylalkyl, mono- or di-alkylaminocarbonylalkyl, arylaminocarbonyl or arylalkylaminocarbonyl, alkylcarbonylamino, arylcarbonylamino or arylalkylcarbonylamino), |
| carbamates | (eg. alkoxycarbonylamino, aryloxycarbonylamino, arylalkyloxycarbonylamino, aminocarbonyloxy, mono- or di-alkylaminocarbonyloxy, arylaminocarbonyloxy or arylalkylaminocarbonyloxy) |
| and ureas | (eg. mono- or di-alkylaminocarbonylamino, arylaminocarbonylamino or arylalkylaminocarbonylamino); |
| nitrogen containing groups such as | |
| amines | (e.g. amino, mono- or dialkylamino, cyclicamino, arylamino, aminoalkyl, mono- or dialkylaminoalkyl), |
| azides, nitriles nitro, | (e.g. cyano, cyanoalkyl), |
| sulfonamides | (e.g. aminosulfonyl, mono- or di-alkylaminosulfonyl, mono- or di-arylaminosulfonyl, alkyl- or aryl-sulfonylamino, alkyl- or aryl-sulfonyl(alkyl)amino, alkyl- or aryl-sulfonyl(aryl)amino); |
| sulfur containing groups such as | |
| thiols, thioethers, sulfoxides, and sulfones | (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl) |
| and heterocyclic groups containing one or more, preferably one, heteroatom, | |
| | (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl). |

Where any of $R_1$ to $R_{15}$ is selected from aryl or from an aryl-containing group such as aryloxy or arylthio, preferred substituent group(s) are selected from halogen, alkyl (substituted or unsubstituted; and where substituted particularly from alkoxyalkyl, hydroxyalkyl, aminoalkyl and haloalkyl), hydroxy, alkoxy, CN, $NO_2$, amines (including amino, mono- and dialkylamino), alkoxycarbonyl, aminocarbonyl, carboxamido, sulfonamido, alkoxycarbonylamino and aryl, and particularly from unsubstituted alkyl, substituted alkyl (including alkoxyalkyl and aminoalkyl), halogen and amines.

In one embodiment, where any of $R_1$ to $R_{15}$ is directly substituted by an alkyl substituent group, or by an alkyl-containing substituent group (such as alkoxy or alkylcarbonylamino for example), then the alkyl moiety of the substituent group directly attached to any of $R_1$ to $R_{15}$ may be further substituted by the substituent groups hereinbefore described and particularly by halogen, hydroxy, alkoxy, CN, amines (including amino, mono- and di-alkyl amino) and aryl.

In a further embodiment, where any of $R_1$ to $R_{15}$ is directly substituted by an aryl substitutent group, or by an aryl-containing substituent group (such as aryloxy or arylaminocarbonylamino for example), then the aryl moiety of the substituent group directly attached to any of $R_1$ to $R_{15}$ may be further substituted by the substituent groups hereinbefore described and particularly by halogen, alkyl (substituted or unsubstituted; and where substituted particularly from alkoxyalkyl, hydroxyalkyl, aminoalkyl and haloalkyl), hydroxy, alkoxy, CN, $NO_2$, amines (including amino, mono- and di-alkylamino), alkoxycarbonyl, aminocarbonyl, carboxamido, sulfonamido, alkoxycarbonylamino and aryl. In a further embodiment, said aryl moiety is substituted by halogen, alkyl (including $CF_3$), hydroxy, alkoxy, CN, amines (including amino, mono- and di-alkyl amino) and $NO_2$. In a further embodiment, said aryl moiety is substituted by unsubstituted alkyl, substituted alkyl (particularly alkoxyalkyl and aminoalkyl), halogen and amines.

The terms "directly substituted" and "directly attached", as used herein, mean that the substituent group is bound directly to any of $R_1$ to $R_{15}$ without any intervening divalent atoms or groups.

In the compounds of formula (I), $R_1$ is selected from alkyl (including branched and unbranched alkyl, substituted and unsubstituted alkyl, and cyclic and acyclic alkyl), alkoxy, aryloxy, alkylthio, arylthio, aryl (including heteroaryl), halogen, CN, $NR_7R_8$ (including $NH_2$, mono-alkylamino and di-alkylamino), $NR_6COR_7$, $NR_6CONR_7R_8$, $NR_6CO_2R_9$ and $NR_6SO_2R_9$.

Where $R_1$ is selected from alkyl, alkoxy and alkylthio, then said alkyl group or the alkyl group of the alkoxy or alkylthio is preferably selected from $C_{1-6}$ alkyl (including branched and unbranched alkyl, substituted and unsubstituted alkyl, and cyclic and acyclic alkyl), preferably saturated $C_{1-6}$ alkyl, and more preferably lower allyl. In one embodiment, $R_1$ is selected from substituted alkyl, particularly haloalkyl (including $CF_3$) and arylalkyl (including heteroarylalkyl), and particularly haloalkyl (including $CF_3$).

Where $R_1$ is selected from $NR_6COR_7$, $NR_6CONR_7R_8$, $NR_6CO_2R_9$ and $NR_6SO_2R_9$, preferably $R_6$ is H or alkyl, and preferably H.

It is preferred that $R_1$ is selected from alkyl, alkoxy, thioalkyl, $NR_7R_8$ (including $NH_2$), $NR_6COR_7$, $NR_6CONR_7R_8$, $NR_6CO_2R_9$ and $NR_6SO_2R_9$, and preferably from $NR_7R_8$ (including $NH_2$), $NR_6COR_7$, $NR_6CONR_7R_8$, $NR_6CO_2R_9$ and $NR_6SO_2R_9$, more preferably from $NR_7R_8$ (including $NH_2$), and more preferably from $NH_2$.

In the compounds of formula (I), $R_2$ is selected from aryl (including heteroaryl) attached via an unsaturated carbon atom. $R_2$ may be substituted or unsubstituted. Preferably, $R_2$ is a 5- or 6membered monocyclic aryl group.

It is preferred that $R_2$ is not an ortho,ortho-disubstituted aryl group. Preferably, $R_2$ is not substituted at an ortho position relative to the point of attachment of the aryl group to the pyrimidine ring.

Preferably, $R_2$ is selected from substituted or unsubstituted heteroaryl attached via an unsaturated carbon atom.

Preferably, $R_2$ is a heteroaryl group which is attached to the pyrimidine ring of formula (I) such that at least one heteroatom is adjacent to the unsaturated carbon atom attached to the pyrimidine ring. Preferably, $R_2$ is an N, O or S-containing heteroaryl group, containing one or more heteroatom(s) selected from N, O and S.

In a preferred embodiment, $R_2$ is selected from furyl (including 2-furyl), thienyl (including 2-thienyl), pyridyl (including 2-pyridyl), thiazolyl (including 2- and 5-thiazolyl), pyrazolyl (including 3-pyrazolyl), triazolyl (including 4-triazolyl), pyrrolyl (including 2-pyrrolyl) and oxazolyl (including 5-oxazolyl). In a further embodiment, $R_2$ is selected from 2-furyl, 2-thienyl, 2-thiazolyl, 2-pyridyl, 3-pyrazolyl, 2-pyrrolyl, 4-triazolyl and 5-oxazolyl. In a further preferred embodiment, $R_2$ is selected from furyl, thienyl, pyridyl, thiazolyl and pyrazolyl, and particularly from 2-furyl, 2-thienyl, 2-thiazolyl, 2-pyridyl and 3-pyrazolyl. In a further embodiment, $R_2$ is selected from furyl, thienyl and pyridyl, preferably 2-furyl, 2-thienyl and 2-pyridyl, and more preferably from 2-furyl.

In a particularly preferred embodiment, $R_2$ is furyl, and preferably 2-furyl.

In the compounds of formula (I), $R_3$ and $R_4$ are independently selected from H, alkyl (including branched and unbranched alkyl, substituted and unsubstituted allyl, and cyclic and acyclic alkyl), halogen, alkoxy, alkylthio, CN and $NR_7R_8$.

Where $R_3$ and $R_4$ are independently selected from alkyl, alkoxy and alkylthio, then said alkyl group or the alkyl group of the alkoxy or alkylthio is preferably selected from $C_{1-6}$ alkyl (including branched and unbranched alkyl, substituted and unsubstituted alkyl, and cyclic and acyclic alkyl), preferably saturated $C_{1-6}$ alkyl, and more preferably lower allyl.

Preferably, $R_3$ and $R_4$ are independently selected from hydrogen.

In the compounds of formula (I), $R_5$ is selected from H, acyclic alkyl (including branched and unbranched alkyl, and substituted and unsubstituted alkyl), $COR_6$, $CONR_7R_8$, $CONR_6NR_7R_8$, $CO_2R_9$ and $SO_2R_9$.

Where $R_5$ is selected from $CONR_7R_8$, $R_7$ and $R_8$ are selected from H, alkyl (including substituted alkyl such as arylalkyl (including heteroarylalkyl)) and aryl (including heteroaryl) or $R_7$ and $R_8$ may be linked to form a heterocyclic ring. In a preferred embodiment, $R_7$ and $R_8$ are selected from H, unsubstituted alkyl, arylalkyl (including heteroarylalkyl) and aryl (including heteroaryl). Said aryl groups may be substituted or unsubstituted. In a preferred embodiment one of $R_7$ and $R_8$ is hydrogen. In a further preferred embodiment, $R_7$ is H and $R_8$ is selected from arylalkyl (including heteroarylalkyl), preferably arylmethyl (including heteroarylmethyl).

Where $R_5$ is selected from acyclic alkyl, it is preferably $C_{1-6}$ acyclic alkyl (including alkenyl and alkynyl). In one embodiment, $R_5$ is selected from $C_{1-6}$ saturated acyclic alkyl, preferably lower alkyl.

In one embodiment, $R_5$ is selected from substituted acyclic alkyl (including saturated acyclic alkyl and alkenyl). Preferred substituents are aryl (including heteroaryl), cycloalkyl, non-aromatic heterocyclyl, $CO_2R_6$, $CONR_7R_8$, $CONR_6NR_7R_8$ and $C(=NR_6)NR_7R_8$, preferably aryl (including heteroaryl) and $CONR_7R_8$, and more preferably aryl (including heteroaryl).

Where $R_5$ is selected from acyclic alkyl substituted by aryl (including heteroaryl), the aryl (including heteroaryl) group may be substituted or unsubstituted, preferably substituted. Preferred aryl groups are discussed below with regard to the group $R_{12}$. Preferably, the aryl-substituted acyclic alkyl is an aryl-substituted methyl group.

In one embodiment, $R_5$ is selected from $(CR_{10}R_{11})_nR_{12}$ wherein n is 1 to 6 (preferably n is 1), $R_{10}$ and $R_{11}$ are independently selected from H, alkyl and aryl, and $R_{12}$ is selected from aryl (including heteroaryl), cycloalkyl, non-aromatic heterocyclic, $CO_2R_6$, $CONR_7R_8$, $CONR_6NR_7R_8$ and $C(=NR_6)NR_7R_8$. Preferably, $R_{12}$ is selected from aryl (including heteroaryl) and $CONR_7R_8$, and more preferably from aryl (including heteroaryl). Preferably $R_{10}$ and $R_{11}$ are independently selected from H and alkyl, more preferably H.

Where $R_{12}$ is selected from $CONR_7R_8$, $R_7$ and $R_8$ are selected from H, alkyl (including substituted alkyl such as arylalkyl (including heteroarylalkyl)) and aryl (including heteroaryl) or $R_7$ and $R_8$ may be linked to form a heterocyclic ring. In one embodiment, $R_7$ and $R_8$ are selected from H, unsubstituted alkyl, arylalkyl (including heteroarylalkyl) and aryl (including heteroaryl). Said aryl groups may be substituted or unsubstituted. In a preferred embodiment one of $R_7$ and $R_8$ is hydrogen.

Where $R_{12}$ is selected from aryl (including heteroaryl), the aryl group may be unsubstituted or substituted, and is preferably substituted. In a preferred embodiment, $R_{12}$ is selected from mono-, di- or tri-substituted aryl (including heteroaryl) groups. Where $R_{12}$ is heteroaryl, $R_{12}$ is preferably selected from mono or bicyclic heteroaryl groups, more preferably from pyridyl (including 2-pyridyl, 3-pyridyl and 4-pyridyl, preferably 2-pyridyl), indolyl (including 2-indolyl, 3-indolyl, 4-indolyl, 5-indolyl, 6-indolyl and 7-indolyl), furyl (including 2-furyl and 3-furyl, preferably 2-furyl), thienyl (including 2-thienyl and 3-thienyl, preferably 2-thienyl), isoindolyl, indolinyl, isoxazolyl, oxazolyl, thiazolyl, pyrazinyl, pyrimidinyl, quinolinyl, benzoxadiazolyl, benzothiadiazolyl, benzotriazolyl, indazolyl, benzodioxolyl and dihydrobenzofuranyl, more preferably from pyridyl (preferably 2-pyridyl), indolyl, furyl (preferably 2-furyl) and thienyl (preferably 2-thienyl), and most preferably from pyridyl (preferably 2-pyridyl), furyl (preferably $^2$-furyl) and thienyl (preferably 2-thienyl). Preferably, $R_{12}$ is selected from phenyl, thienyl, furyl and pyridyl, more preferably from phenyl, 2-thienyl, 2-furyl and 2-pyridyl.

In one embodiment, $R_{12}$ is selected from mono-, di- or tri-substituted aryl (including heteroaryl) groups represented by the formula $Ar(R_{13})_a(R_{14})_b(R_{15})_c$ wherein Ar is an aryl (including heteroaryl) group, preferably selected from the preferred aryl groups described above for $R_{12}$; wherein $R_{13}$, $R_{14}$ and $R_{15}$ are substituent group(s), the same or different; and wherein a, b and c are 0 or 1 such that $a+b+c \geq 1$.

The substituent groups $R_{13}$, $R_{14}$ and $R_{15}$ may be selected from any of the substituent groups described herein above.

In a preferred embodiment, $R_{13}$, $R_{14}$ and $R_{15}$ are selected from $NR_7R_8$ (including $NH_2$, and $NHR_7$) alkyl (substituted or unsubstituted; preferably $C_{1-6}$ acyclic alkyl), alkoxy (including fluoroalkoxy), halogen (including F, Cl, Br and I), $NO_2$, CN, hydroxy, NHOH, CHO, $CONR_7R_8$, $CO_2R_7$, $NR_6COR_7$ (preferably $NHCOR_7$), $NR_6CO_2R_9$ (preferably $NHCO_2R_9$), $NR_6SO_2R_9$ (preferably $NHSO_2R_9$), $OCO_2R_9$ and aryl (including heteroaryl).

In a more preferred embodiment, $R_{13}$, $R_{14}$ and $R_{15}$ are selected from $NR_7R_8$ (including $NH_2$ and $NHR_7$), alkyl (substituted or unsubstituted; and preferably $C_{1-6}$ acyclic saturated alkyl) and halogen (preferably P or Cl, particularly F).

In a particularly preferred embodiment, $R_{13}$, $R_{14}$ and $R_{15}$ are selected from $NR_7R_8$ (including $NH_2$ and $NHR_7$, preferably $NH_2$) and allyl (substituted or unsubstituted; preferably $C_{1-6}$ acyclic saturated alkyl).

Where $R_{13}$, $R_{14}$ and $R_{15}$ are selected from substituted alkyl, said alkyl is preferably selected from alkoxyalkyl, hydroxyalkyl, aminoalkyl (including $NH_2$-alkyl, mono-alkylaminoalkyl and di-alkylaminoalkyl), haloalkyl (particularly fluoroalkyl (including $CF_3$)), cyanoalkyl, alkylthioalkyl, alkylcarboxyaminoalkyl, alkoxycarbonylaminoalkyl and alkylsulfonylamino, more preferably from alkoxyalkyl, hydroxyalkyl, aminoalkyl and haloalkyl (particularly fluoroalkyl (including $CF_3$)) and most preferably from alkoxyalkyl and aminoalkyl.

In one embodiment, the substituent groups $R_{13}$, $R_{14}$ and $R_{15}$ are selected from halogen, alkyl (including $CF_3$), hydroxy, alkoxy, alkylthio, CN, amines (including amino, mono- and di-alkyl amino) and $NO_2$.

In a preferred embodiment, $R_5$ is selected from H and substituted acyclic alkyl, preferably wherein said acyclic alkyl is substituted by aryl (including heteroaryl) or $CONR_7R_8$.

In the compounds of formula (I), $R_6$, $R_7$, $R_8$, $R_{10}$ and $R_{11}$ are independently selected from H, alkyl (including branched and unbranched alkyl, substituted and unsubstituted alkyl, cyclic and acyclic alkyl) and aryl (including heteroaryl) or where $R_7$ and $R_8$ are in any $NR_7R_8$ group $R_7$ and $R_8$ may be linked to form a heterocyclic group, or where $R_6$, $R_7$ and $R_8$ are in a $(CONR_6NR_7R_8)$ group, $R_6$ and $R_7$ may be linked to form a heterocyclic group.

In the compounds of formula (I), $R_9$ is selected from alkyl (including branched and unbranched alkyl, substituted and unsubstituted alkyl, cyclic and acyclic alkyl) and aryl (including heteroaryl).

Where $R_6$ to $R_{11}$ are independently selected from alkyl, preferably $R_6$ to $R_{11}$ are selected from $C_{1-6}$ alkyl, preferably $C_{1-6}$ saturated alkyl and more preferably from lower alkyl.

Where $R_7$ and $R_8$, or $R_6$ and $R_7$, are linked to form a heterocyclic ring said heterocyclic ring may be saturated, partially unsaturated or aromatic, and is preferably saturated. Said heterocyclic ring is preferably a 5, 6 or 7-membered ring, preferably a 5 or 6-membered ring, and may contain one or more firer heteroatom(s) preferably selected from N, O and S.

In a preferred embodiment, $R_1$ is $NH_2$, $R_2$ is 2-furyl, $R_3$ and $R_4$ are H and $R_5$ is arylmethyl (including heteroarylmethyl).

In a particularly preferred embodiment of the invention, the compound of formula (I) is 7-(2-fluorobenzyl)-4-(2-furyl)-7H-pyrrolo[2,3-d]pyrimidine-2-amine.

Where chiral the compounds of formula (I) may be in the form of a racemic mixture of pairs of enantiomers or in enantiomerically pure form.

According to a further aspect of the present invention there is provided a method of treating or preventing a disorder in which the blocking of purine receptors, particularly adenosine receptors and more particularly adenosine $A_{2A}$ receptors, may be beneficial, the method comprising administration to a subject in need of such treatment an effective dose of a compound of formula (I) or a pharmaceutically acceptable salt or prodrug thereof.

The disorder may be caused by the hyperfunctioning of the purine receptors.

The present invention may be employed in respect of a human or animal subject, more preferably a mammal, more preferably a human subject.

The disorders of particular interest are those in which the blocking of purine receptors, partiucularly adenosine receptors and more particularly adenosine $A_{2A}$ receptors, may be beneficial. These may include movement disorders such as Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the blocking of purine receptors, may be of benefit include progressive supernuclear palsy, Huntingtons disease, multiple system atrophy, corticobasal degeneration, Wilsons disease, Hallerrorden-Spatz disease, progressive pallidal atrophy, Doparesponsive dystonia-Parkinsonism, spasticity or other disorders of the basal ganglia which result in abnormal movement or posture. The present invention may also be effective in treating Parkinson's with on-off phenomena; Parkinson's with freezing (end of dose deterioration); and Parkinson's with prominent dyskinesias.

The compounds of formula (I) may be used or administered in combination with one or more additional drugs useful in the treatment of movement disorders, such as L-DOPA or a dopamine agonist, the components being in the same formulation or in separate formulations for administration simultaneously or sequentially.

Other disorders in which the blocking of purine receptors, particularly adenosine receptors and more particularly adenosine $A_{2A}$ receptors may be beneficial include acute and chronic pain; for example neuropathic pain, cancer pain, trigeminal neuralgia, migraine and other conditions associated with cephalic pain, primary and secondary hyperalgesia, inflammatory pain, nociceptive pain, tabes dorsalis, phantom limb pain, spinal cord injury pain, central pain, post-herpetic pain and HIV pain; affective disorders including mood disorders such as bipolar disorder, seasonal affective disorder, depression, manic depression, atypical depression and monodepressive disease; central and peripheral nervous system degenerative disorders including corticobasal degeneration, demyelinating disease (multiple sclerosis, disseminated sclerosis), Freidrich's ataxia, motoneurone disease (amyotrophic lateral sclerosis, progressive bulbar atrophy), multiple system atrophy, myelopathy, radiculopathy, peripheral neuropathy (diabetic neuropathy, tabes dorsalis, drug-induced neuropathy, vitamin deficiency), systemic lupus erythamatosis, granulomatous disease, olivoponto-cerebellar atrophy, progressive pallidal atrophy, progressive supranuclear palsy, spasticity; schizophrenia and related pyshoses; cognitive disorders including dementia, Alzheimers Disease, Frontotemporal dementia, multi-infarct dementia, AIDS dementia, dementia associated with Huntingtons Disease, Lewy body dementia, senile dementia, age-related memory impairment, cognitive impairment associated with dementia, Korsakoff syndrome, dementia pugilans; attention disorders such as attention-deficit hyperactivity disorder (ADHD), attention deficit disorder, minimal brain dysfunction, brain-injured child syndrome, hyperkinetic reaction childhood, and hyperactive child syndrome; central nervous system injury including traumatic brain injury, neurosurgery (surgical trauma), neuroprotection for head injury, raised intracranial pressure, cerebral oedema, hydrocephalus, spinal cord injury; cerebral ischaemia including transient ischaemic attack, stroke (thrombotic stroke, ischaemic stroke, embolic stroke, haemorrhagic stroke, lacunar stroke) subarachnoid haemorrhage, cerebral vasospasm, neuroprotection for stroke, peri-natal asphyxia, drowning, cardiac arrest, subdural haematoma; myocardial ischaemia; muscle ischaemia; sleep disorders such as hypersomnia and narcolepsy; eye disorders such as retinal ischaemia-reperfusion injury and diabetic neuropathy; cardiovascular disorders such as claudication and hypotension; and diabetes and its complications.

According to a further aspect of the present invention there is provided use of a compound of formula (I) or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of formula (I) or a pharmaceutically acceptable salt or prodrug thereof.

According to a further aspect of the invention there is provided use of a compound of formula (I) or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of formula (I) or a pharmaceutically acceptable salt or prodrug thereof.

The medicament for or method of neuroprotection may be of use in the treatment of subjects who are suffering from or at risk from a neurodegenerative disorder, such as a movement disorder.

According to a further aspect of the invention, there is provided for use in therapy a compound of formula (I), or a pharmaceutically acceptable salt or prodrug thereof.

According to a further aspect of the invention, there is provided a compound of formula (I), or a pharmaceutically acceptable salt or prodrug thereof, per se, other than:

(i) compounds wherein $R_2$ is selected from pyrrolopyrimidines; and (ii) compounds wherein $R_1$ is selected from methyl, phenyl and (methyl)phenyl, $R_2$ is selected from phenyl (substituted or unsubstituted) and $R_5$ is selected from methyl and methanesulfonyl, preferably compounds wherein $R_1$ is selected from methyl and phenyl (substituted or unsubstituted), $R_2$ is selected from phenyl (substituted or unsubstituted) and $R_5$ is selected from methyl and methanesulfonyl, and more preferably wherein $R_1$ is selected from methyl and phenyl (substituted or unsubstituted) and $R_2$ is selected from phenyl (substituted or unsubstituted).

According to a further aspect of the invention, there is provided a compound of formula (I), or a pharmaceutically acceptable salt or prodrug thereof, per se, wherein $R_2$ is selected from heteroaryl, other than compounds wherein $R_2$ is selected from pyrrolopyrimidines.

In a preferred embodiment, there is provided a compound of formula (I), or a pharmaceutically acceptable salt or prodrug thereof, per se, wherein $R_2$ is selected from 5- or 6-membered monocyclic heteroaryl groups.

According to a further aspect of the invention, there is provided a method of preparing the novel compounds of the present invention. Compounds of formula (I) may be prepared according to conventional synthetic methods, such as set out in Reaction Scheme 1.

Reaction Scheme 1

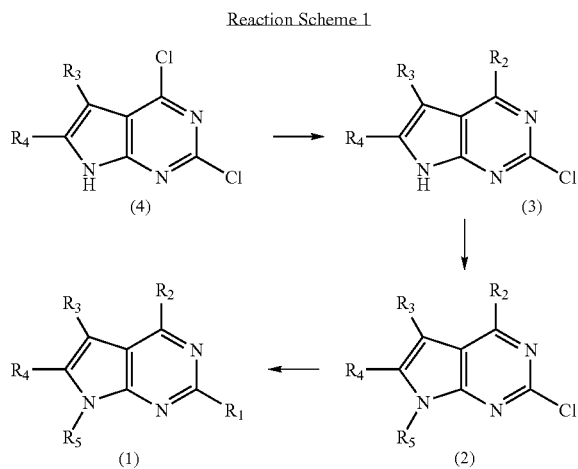

Compounds of formula (1) where $R_1$ is alkoxy, aryloxy, alkylthio, arylthio, CN or $NR_7R_8$ may be prepared from compounds of formula (2) by standard methods such as nucleophilic displacement using an appropriate nucleophilic reagent such as an alcohol, thiol, cyanide or amine ($HNR_7R_8$) in the presence of a suitable base if required.

Compounds of formula (1) where $R_1$ is $NR_6COR_7$, $NR_6CO_2R_9$ or $NR_6SO_2R_9$, wherein $R_6$ is H, alkyl or aryl, may be prepared from compounds of formula (1) where $R_1$ is $NR_7R_8$, wherein $R_7$ is H and $R_8$ is H, alkyl or aryl, by standard methods such as treatment with an appropriate acid chloride ($R_7COCl$), chloroformate ($ClCO_2R_9$) or sulphonyl chloride ($R_9SO_2Cl$) in the presence of a suitable base such as triethylamine.

Compounds of formula (1) where $R_1$ is $NR_6CONR_7R_8$ wherein $R_6$ is H, alkyl or aryl, may be prepared from compounds of formula (1) where $R_1$ is $NR_7R_8$, wherein $R_7$ is H and $R_8$ is H, alkyl or aryl, by standard methods such as treatment with an appropriate isocyanate ($R_7NCO$ or $R_8NCO$) or carbamoyl chloride ($R_7R_8NCOCl$) in the presence of a suitable base such as triethylamine if required.

Compounds of formula (1) where $R_1$ is $NH_2$ may be prepared from compounds of formula (1) where $R_1$ is $NR_7R_8$, wherein $R_7$ is H and Rs is a suitable protecting group such as a 3,4-dimethoxybenzyl group, by standard methods such as treatment with TFA.

Compounds of formula (2) where $R_5$ is alkyl (including arylalkyl, heteroarylalkyl and $(CR_{10}R_{11})_nR_{12}$) may be prepared from a compound of formula (3) by standard methods such as reaction with an appropriate alkyl halide, or substituted alkyl halide in the presence of a suitable base such as sodium hydride.

Compounds of formula (2) where $R_5$ is $(CR_{10}R_{11})_nR_{12}$ and $R_{12}$ is $CONR_7R_8$ or $CONR_6NR_7R_8$ may be prepared from compounds of formula (2) where $R_5$ is $(CR_{10}R_{11})_nR_{12}$ and $R_{12}$ is $CO_2R_6$ by standard methods such as direct reaction with an appropriate amine or hydrazine or by initial hydrolysis of the ester group $CO_2R_6$ to a carboxylic acid followed by reaction with an appropriate amine or hydrazine in the presence of a standard coupling reagent such as DCC.

Compounds of formula (2) where $R_5$ is $(CR_{10}R_{11})_nR_{12}$, wherein $R_{12}$ is $C(=NR_6)NR_7R_8$ may be prepared from compounds of formula (2) where $R_5$ is $(CR_{10}R_{11})_nR_{12}$ wherein $R_{12}$ is CN by standard methods such as treatment with an appropriate amine in the presence of trimethyl aluminium.

Compounds of formula (2) where $R_5$ is $(CR_{10}R_{11})_nR_{12}$, wherein $R_{12}$ is $CO_2R_6$ or CN may be prepared from compounds of formula (3) by standard methods such as treatment with an appropriate substituted alkyl halide in the presence of a suitable base such as sodium hydride.

Compounds of formula (2) where $R_5$ is $CONR_7R_8$ or $CONR_6NR_7R_8$ may be prepared from compounds of formula (3) by standard methods such as treatment with an appropriate isocyanate ($R_7NCO$ or $R_8NCO$) or carbamoyl chloride ($R_7R_8NCOCl$ or $R_7R_8NR_6NCOCl$).

Compounds of formula (2) where $R_5$ is $COR_6$, $CO_2R_9$ or $SO_2R_9$ may be prepared from compounds of formula (3) by standard methods such as treatment with an appropriate acid chloride ($R_6COCl$), chloroformate ($ClCO_2R_9$) or sulphonyl chloride ($R_9SO_2Cl$) in the presence of a suitable base such as triethylamine.

Compounds of formula (3) are prepared from compounds of formula (4) by standard methods such as aryl or heteroaryl coupling reactions. Suitable aryl or heteroaryl coupling reactions would include reaction with an appropriate aryl or heteroaryl trialkylstannane derivative, an aryl or heteroarylboronic acid or boronic ester derivative, or an aryl or heteroarylzinc halide derivative in the presence of a suitable catalyst such as a palladium complex. Compounds of formula (4) are either known in the literature or are prepared by methods which are analogous to those described in the literature.

In certain cases it may be advantageous to prepare a compound of formula (2) where $R_5$ is selected to perform the function of a protecting group, for example a suitable protecting group would be a benzyl group or substituted benzyl group such as a 3,4dimethoxybenzyl group or a trimethylsilylethoxymethyl group. Compounds of this nature may prepared as described above and converted to compounds of formula (1), where $R_5$ is a protecting group, as described above. The protecting group $R_5$ may be then be removed by standard methods such as treatment with, for example, TFA or tetra-n-butylammonium fluoride to give a compound of formula (1) where $R_5$ is H. Compounds of formula (1) where $R_5$ is H may then be used to prepare other compounds of formula (1), where $R_5$ is as previously defined, by the methods described above.

In certain cases it may be advantageous to prepare compounds of formula (1) where $R_5$ is alkyl (including arylalkyl, heteroarylalkyl and $(CR_{10}R_{11})_nR_{12}$ from compounds of formula (1) where $R_5$ is H by the methods described above.

Other compounds of formula (1) may be prepared by standard methods such as those illustrated in Reaction Scheme 2.

Reaction Scheme 2

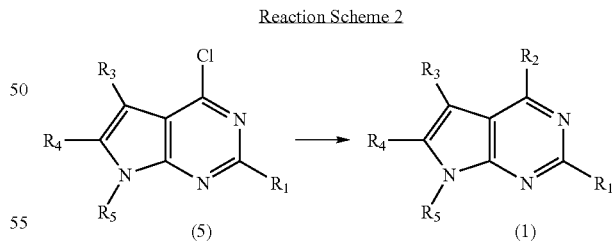

Compounds of formula (1) where $R_1$ is alkyl or aryl may be prepared from compounds of formula (5) where $R_1$ is alkyl or aryl by standard methods such as aryl or heteroaryl coupling reactions as described above. Compounds of formula (5) where $R_1$ is alkyl or aryl are either known in the literature or may be prepared by methods analogous to those described in the literature.

Compounds of formula (1) where $R_3$ and $R_4$ are H, alkyl, halogen, alkoxy, alkylthio, CN or $NR_7R_8$ may be prepared by the methods described above. Suitable intermediates such as compounds of formula (4) and (5) where $R_3$ and $R_4$ are as described above, are either known in the literature or are prepared by methods which are analogous to those described in the literature.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

The pharmaceutical compositions employed in the present invention comprise a compound of formula (I), or pharmaceutically acceptable salts or prodrugs thereof, and may also contain a pharmaceutically acceptable carrier and optionally other therapeutic ingredients known to those skilled in the art. The term, "pharmaceutically acceptable salts", refers to salts prepared from pharmaceutically acceptable non-toxic acids including inorganic acids and organic acids.

Where the compounds of formula (I) are basic, salts may be prepared from pharmaceutically acceptable non-toxic acids including inorganic and organic acids. Such acids include acetic, benzenesulfonic, benzoic, camphorsulfonic, citric, ethenesulfonic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

Any suitable route of administration may be employed for providing the patient with an effective dosage of a compound of formula (I). For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of formula (I) may also be administered by controlled release means and/or delivery devices such as those described in U.S. Pat. Nos.: 3,845,770; 3,916,899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

EXAMPLES

Synthetic Examples

The invention is illustrated with reference to the following Examples, as set out in Table 1.

TABLE 1

| Example | Structure | Compound Name |
|---|---|---|
| 1 | 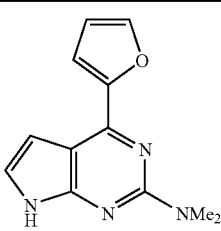 | N,N-dimethyl-4-(2-furyl)-1H-pyrrolo[2,3-d]pyrimidine-2-amine |

TABLE 1-continued

| Example | Structure | Compound Name |
|---|---|---|
| 2 | 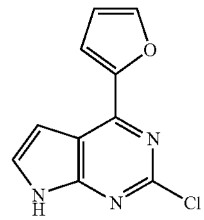 | 2-chloro-4-(2-furyl)-1H-pyrrolo[2,3-d]pyrimidine |
| 3 | 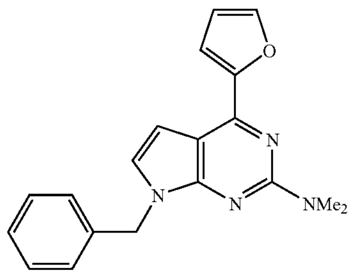 | 7-benzyl-N,N-dimethyl-4-(2-furyl)-7H-pyrrolo[2,3-d]pyrimidine-2-amine |
| 4 | 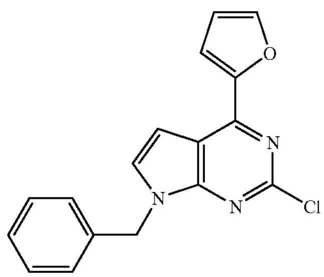 | 7-benzyl-2-chloro-4-(2-furyl)-7H-pyrrolo[2,3-d]pyrimidine |
| 5 | 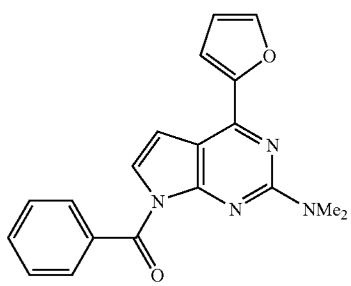 | 7-benzoyl-N,N-dimethyl-4-(2-furyl)-7H-pyrrolo[2,3-d]pyrimidine-2-amine |
| 6 | 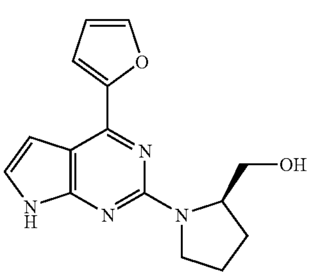 | (2R)-2-(2-hydroxymethylpyrrolidin-1-yl)-4-(2-furyl)-1H-pyrrolo[2,3-d]pyrimidine |

TABLE 1-continued

| Example | Structure | Compound Name |
|---|---|---|
| 7 | 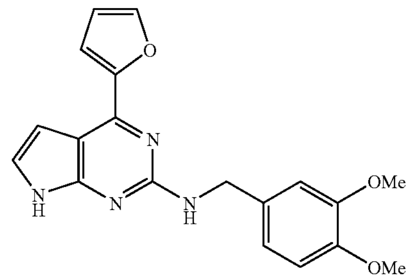 | N-(3,4-dimethoxybenzyl)-4-(2-furyl)-1H-pyrrolo[2,3-d]pyrimidine-2-amine |
| 8 | 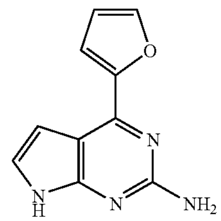 | 4-(2-furyl)-1H-pyrrolo[2,3-d]pyrimidine-2-amine |
| 9 | 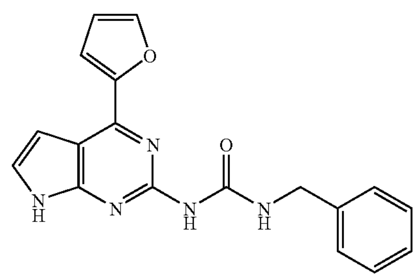 | N-benzyl-N'-(4-(2-furyl)-1H-pyrrolo[2,3-d]pyrimidin-2-yl)urea |
| 10 | 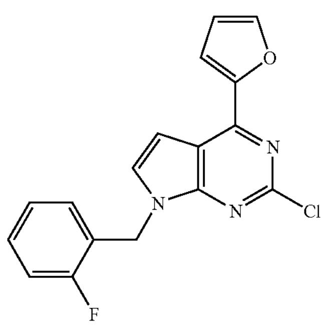 | 2-chloro-7-(2-fluorobenzyl)-4-(2-furyl)-7H-pyrrolo[2,3-d]pyrimidine |
| 11 | 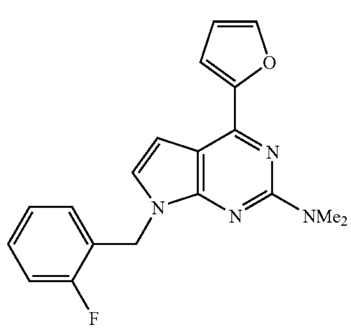 | N,N-dimethyl-7-(2-fluorobenzyl)-4-(2-furyl)-7H-pyrrolo[2,3-d]pyrimidine-2-amine |

TABLE 1-continued

| Example | Structure | Compound Name |
|---|---|---|
| 12 | 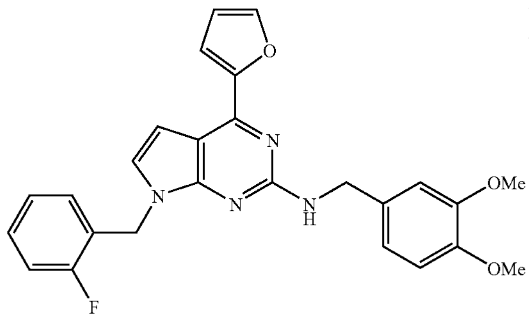 | N-(3,4-dimethoxybenzyl)-7-(2-fluorobenzyl)-4-(2-furyl)-7H-pyrrolo[2,3-d]pyrimidine-2-amine |
| 13 | 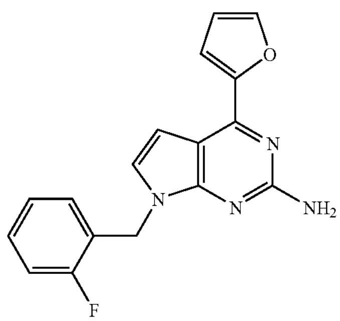 | 7-(2-fluorobenzyl)-4-(2-furyl)-7H-pyrrolo[2,3-d]pyrimidine-2-amine |

The syntheses of the above Examples is described with reference to the following general synthetic Methods. The analytical data for the Examples, together with the Method of synthesis used is given in Table 2.

Synthetic Methods

Method A

2-Chloro-4-(2-furyl)-1H-pyrrolo[2,3-d]pyrimidin (Example 2)

A solution of 2,4-dichloro-1H-pyrrolo[2,3-d]pyrimidine (4.1 g, 21.8 mmol) in DMF (20 mL) was treated with PdCl$_2$(PPh$_3$)$_2$ (772 mg, 0.17 mmol) and 2-(tributylstannyl)-furan (6.9 mL, 21.8 mmol), stirred at room temperature for 16 h, diluted with diethyl ether and filtered to give the title compound (2.94 g, 61%) as a pale orange solid.

Method B 2-chloro-7-(2-fluorobenzyl)-4-(2-furyl)-7H-pyrrol[2,3-d]pyrimidine (Example 10)

A solution of 2-chloro-4-(2-furyl)-1H-pyrrolo[2,3-d]pyrimidine (219 mg, 1 mmol) in DMF (2 mL) at 0° C. was treated with NaH (40 mg, 60%, 1 mmol), stirred for 20 min, treated with 2-fluorobenzyl bromide (120 µL, 1 mmol), stirred at room temperature for 1 h, quenched with water, extracted with EtOAc, dried (MgSO$_4$), concentrated in vacuo and purified by chromatography (EtOAc:Heptane, 1:4) to give the title compound (250 mg, 76%) as a cream solid.

Method C

N-(3,4-dimethoxybenzyl)-7-(2-fluorobenzyl)-4-(2-furyl)-7H-pyrrolo[2,3-d]pyrimidine-2-amine (Example 12)

A solution of 2-chloro-7-(2-fluorobenzyl)4(2-furyl)-7H-pyrrolo[2,3-d]pyrimidine (254 mg, 0.78 mmol) in N-methylpyrrolidone (2 mL) was treated with veratrylamine (0.25 mL, 1.66 mmol), heated to 100° C. for 16 h and purified by chromatography (Heptane:EtOAc, 4:1) to give the title compound (316 mg, 88%) as a cream solid.

Method D 7-(2-fluorobenzyl)-4-(2-furyl)-7H-pyrrolo[2,3-d]pyrimidine-2-amine (Example 13)

A solution of N-(3,4-dimethoxybenzyl)-7-(2-fluorobenzyl)4-(2-furyl)-7H-pyrrolo[2,3-d]pyrimidine-2-amine (110 mg, 0.24 mmol) in TFA (1 mL) was heated to 50° C. for 3 h, concentrated in vacuo, treated with saturated NaHCO$_3$, extracted with EtOAc, dried (MgSO$_4$), concentrated in vacuo, purified by chromatography (EtOAc:Heptane, 1:4) and recrystallised (EtOAc) to give the title compound (38 mg, 51%) as a cream solid.

Method E

7-Benzoyl-N,N-dimethyl-4-(2-furyl)-7H-pyrrolo[2,3-d]pyrimidine-2-amine (Example 5)

A solution of N,N-dimethyl-4-(2-furyl)-1H-pyrrolo[2,3-d]pyrimidine-2-amine (181 mg, 0.8 mmol) in THF (3 mL)

was treated with Et₃N, (111 µL, 0.8 mmol), benzoyl chloride (93 µL, 0.8 mmol) and a catalytic amount of DMAP, stirred at room temperature for 16 h, quenched with water, extracted with EtOAc, dried (MgSO₄), concentrated in vacuo and purified by chromatography (EtOAc:Heptane, 1:9 then Heptane:DCM, 2:1) to give the title compound (76 mg) as a yellow solid.

Method F

N-benzyl-N'-(4-(2-furyl)-1H-pyrrolo[2,3-d]pyrimidin-2-yl)urea (Example 9)

A solution of 4-(2-furyl)-1H-pyrrolo[2,3-d]pyrimidine-2-amine (192 mg, 0.96 mmol) in THF (3 mL) was treated with benzyl isocyanate (118 µL, 0.96 mmol), stirred at room temperature for 16 h and the resulting solid filtered and washed with EtOAc to give the title compound (61 mg, 19%) as a yellow solid.

Method G

2,4-Dichloro-7-(2-trimethylsilylethoxymethyl)-7H-pyrrolo[2,3-d]pyrimidine

A solution of 2,4-dichloro-1H-pyrrolo[2,3-d]pyrimidine (542 mg, 2.58 mmol) in MeCN (20 mL) was treated with NaH (113 mg, 2.84 mmol), stirred for 1 h, treated with trimethylsilylethyl chloride (502 µL, 2.84 mmol), stirred at room temperature for 3 h, poured into water, extracted with EtOAc, dried (MgSO₄) and concentrated in vacuo to give the title compound (913 mg, 104%) which was used crude in the next reaction.

Method H

N,N-Dimethyl-4-(2-furyl)-1H-pyrrolo[2,3-d]pyrimidine-2-amine (Example 1)

A solution of N,N-dimethyl4-(2-furyl)-7-(2-trimethylsilylethoxymethyl)-7H-pyrrolo[2,3-d]pyrimidine-2-amine (370 mg, 0.97 mmol) in THF (3 mL) was treated with tetrabutylammonium fluoride (1 ml, 1-M in THF, 1 mmol), refluxed for 36 h, poured into water, extracted with EtOAc, dried (MgSO₄), concentrated in vacuo and purified by chromatography (EtOAc:Heptane, 1:9, alumina) to give the title compound (47 mg, 21%) as a yellow solid.

2-Chloro-4-(2-furyl)-7-(2-trimethylsilylethoxymethyl)-7H-pyrrolo[2,3-d]pyrimidine This was prepared from 2,4-dichloro-7-(2-trimethylsilylethoxymethyl)-7H-pyrrolo[2,3-d]pyrimidine by method A and the title compound (207 mg, 21%) isolated as a cream solid.

N,N-Dimethyl-4-(2-furyl)-7-(2-trimethylsilylethoxymethyl)-7H-pyrrolo[2,3-d]pyrimidine-2-amine This was prepared from 2-chloro-4-(2-furyl)-7-(2-trimethylsilylethoxymethyl)-7H-pyrrolo[2,3-d]pyrimidine by method C and the title compound (409 mg, 77%) isolated as a white solid.

TABLE 2

| Example | Method | Yield (%) | Physical Data |
|---|---|---|---|
| 1 | H | 21 | mp 196.9–197.1 °C.; NMR $\delta_H$ (400 MHz, CDCl₃) 3.27 (6H, s), 6.57–6.60 (1H, m), 6.83–6.86 (1H, m), 6.93– 6.97 (1H, m), 7.31 (1H, d, J 4.0 Hz), 7.65–7.68 (1H, m), 8.84 (1H, s) |
| 2 | A | 61 | mp 265.8–266.3 °C.; IR $v_{max}$ (Nujol)/cm⁻¹ 3199, 3108, 2924, 2854, 1593, 1530 and 1462; NMR $_H$ (400 MHz, DMSO) 6.79–6.82 (1H, m), 6.98–6.99 (1H. m), 7.50 (1H, d, J 3.5 Hz), 7.67 (1H, t, J 3.5 Hz), 8.08 (1H, d. J 1.0 Hz), 12.4 (1H, s) |
| 3 | B | | mp 91.7–92.3 °C.; IR $v_{max}$ (Nujol)/cm⁻¹ 3020, 2924, 2854, 1613, 1582, 1542, 1452, 1395 and 733 ; NMR$_{\delta H}$ (400 MHz, CDCl₃) 3.27 (6H, s), 5.31 (2H, s), 6.55–6.57 (1H, m), 6.80 (1H, d, J 3.5 Hz), 6.81 (1H, d, J 4.0 Hz), 7.23–7.34 (6H, m), 7.63–7.65 (1H, m); |
| 4 | B | | IR $v_{max}$ (Nujol)/cm⁻¹ 3116, 3064, 3032, 2931, 1600, 1565, 1509, 1328, 1256, 1151 and 920; NMR $\delta_H$ (400 MHz, CDCl₃) 5.43 (2H, s), 6.61–6.65 (1H, m), 7.01 (1H, d, J 3.5 Hz), 7.15 (1H, d, J 3.5 Hz), 7.21–7.37 (5H, m), 7.47 (1H, dd, J 3.5, 1.0 Hz), 7.69–7.71 (1H, m) |
| 5 | E | | mp 108.3–109.1 °C.; NMR $\delta_H$ (400 MHz, CDCl₃) 2.89 (6H, s), 6.57–6.60 (1H, m), 7.05 (1H, d, J 4.0 Hz), 7.28–7.29 (1H, m), 7.43–7.48 (2H, m), 7.53–7.59 (2H, m), 7.66–7.67 (1H, m), 7.75–7.79 (2H, m); Anal. Calcd for C₁₉H₁₆N₄O₂ + 0.3 H₂O: C, 67.56; H, 4.95, N, 16.59. Found: C, 67.48; H, 4.72; N, 16.45; .M/Z 333 (M + H)⁺. |
| 6 | C | 64 | mp 174.8–175.6 °C.; IR $v_{max}$ (Nujol)/cm⁻¹ 3094, 2752, 1611, 1560, 1518 and 1467; NMR $\delta_H$ (400 MHz, DMSO) 1.81–2.04 (2H, m), 3.26–3.36 (2H, m), 3.56–3.47 (1H, m), 3.47–3.62 (2H, m), 3.69–3.76 (1H, m), 4.11–4.24 (1H, m), 5.01 (1H, s), 6.66–6.69 (1H, m), 6.71–6.74 (1H, m), 7.11 (1H, dd, J 3.5, 2.0 Hz), 7.30 (1H, dd, J 3.5, 1.0 Hz), 7.96–7.97 (1H, m), 11.41 (1H, s). |
| 7 | C | 82 | mp 154.8–154.9 °C.; IR $v_{max}$ (Nujol)/cm⁻¹ 3459, 3416, 3142, 1623, 1593, 1482, 1467, 1266 and 742; NMR $\delta_H$ (400 MHz, DMSO) 3.69 (3H, s), 3.71 (3H, s), 4.47 (2H, d, J 6.0 Hz), 6.65–6.67 (1H, m), 6.71– 6.72 (1H, m), 6.83–6.91 (2H, m), 7.03–7.09 (3H, m), 7.27 (1H, d, J 2.5 Hz), 7.94–7.96 (1H, m), 11.27 (1H, s); Anal. Calcd for C₁₉H₁₈N₄O₃ + 2 H₂O: C, 59.06; H, 5.749, N, 14.50. Found: C, 59.07; H, 5.74; N, 14.19. |
| 8 | D | 83 | mp 213.5–214.5 °C.; IR $v_{max}$ (Nujol)/cm⁻¹ 3448, 3287, 3188, 3133, 3069, 2924, 2854, 1625, 1556 and 1468; NMR $\delta_H$ (400 MHz, DMSO) |

TABLE 2-continued

| Example | Method | Yield (%) | Physical Data |
|---|---|---|---|
| 9 | F | 19 | 6.10 (2H, s), 6.64–6.67 (1H, m), 6.69–6.71 (1H, m), 7.09 (1H, dd, J 3.5, 2.5 Hz), 7.21–7.24 (1H, d, 72.5 Hz), 7.95 (1H, s), 11.22 (1H, s). IR $v_{max}$ (Nujol)/cm$^{-1}$ 3208, 3140, 2730, 1668, 1603, 1557, 1463, 1376 and 1363; NMR $\delta_H$ (400 MHz, DMSO) 4.51 (2H, d, J 5.5 Hz), 6.68–6.70 (1H, m), 6.82–6.85 (1H, m), 7.07 (1H, d, J 3.5 Hz), 7.27–7.33 (1H, m), 7.35–7.44 (5H, m), 7.95 (1H, d, J 1.0 Hz), 9.42 (1H, s), 9.86 (1H, t, J 5.5 Hz), 11.88 (1H, s). |
| 10 | B | 76 | mp 126.8–127.1 °C.; IR $v_{max}$ (Nujol)/cm$^{-1}$ 2923, 2854, 1601, 1547, 1458, 1376, 1256, 920 and 733; NMR $\delta_H$ (400 MHz, DMSO) 5.52 (2H, s), 6.80–6.83 (1H, m), 7.06 (1H, d, J 3.5 Hz), 7.10–7.19 (2H, m), 7.22–7.28 (1H, m), 7.35–7.41 (1H, m), 7.52 (1H, d, J 3.5 Hz), 7.71 (1H, d, J 3.5 Hz), 8.10 (1H, s); Anal. Calcd for $C_{17}H_{11}ClN_3O + 0.25 H_2O$: C, 61.46; H, 3.49, N, 12.65. Found: C, 61.31; H, 3.31; N, 12.37. |
| 11 | C | 86 | mp 115.1–115.2 °C.; NMR $\delta_H$ (400 MHz, DMSO) 3.18 (6H, s), 5.35 (2H, s), 6.70–6.75 (2H, m), 7.10–7.27 (4H, m), 7.30–7.38 (2H, m), 7.97 (1H, s); Anal. Calcd for $C_{19}H_{17}FN_4O + 0.1 H_2O$: C, 67.48; H, 5.13, N, 16.57. Found: C, 67.51; H, 5.10; N, 16.13; M/Z 336 M$^+$. |
| 12 | C | 88 | IR $v_{max}$ (Nujol)/cm$^{-1}$ 3252, 3112, 2924, 2854, 1582, 1515 and 1464; NMR $\delta_H$ (400 MHz, DMSO) 3.67 (3H, s), 3.69 (3H, s), 4.46 (2H, d, J 6.5 Hz), 5.33 (2H, s), 6.69–6.75 (2H, m), 6.79 (1H, d, J 8.5 Hz), 6.89 (1H, d, J 8.0 Hz), 6.97–7.09 (3H, m), 7.14–7.37 (5H, m), 7.96 (1H, s); Anal. Calcd for $C_{26}H_{23}FN_4O_3$: C, 68.11; H, 5.06, N, 12.21. Found: C, 68.14; H, 5.08; N, 12.20. |
| 13 | D | 51 | IR $v_{max}$ (Nujol)/cm$^{-1}$ 3329, 3193, 2924, 1649, 1577 and 1552; NMR $\delta_H$ (400 MHz, DMSO) 5.34 (2H, s), 6.26 (2H, s), 6.70–6.73 (1H, m), 6.77 (1H, d, J 3.5 Hz), 6.95 (1H, t, J 8.0 Hz), 7.09–7.18 (2H, m), 7.19–7.28 (2H, m), 7.30–7.37 (1H, m), 7.96 (1H, s). |

Adenosine Receptor Binding

Binding Affinities at hA$_{2A}$ Receptors

The compounds were examined in an assay measuring in vitro binding to human adenosine A$_{2A}$ receptors by determining the displacement of the adenosine A$_{2A}$ receptor selective radioligand [$^3$H]-CGS 21680 using standard techniques. The results are summarised in Table 3.

TABLE 3

| Example | K$_i$(nM) |
|---|---|
| Example 1 | 60 |
| Example 8 | 272 |
| Example 13 | 16 |

Evaluation of Potential Anti-Parkinsonian Activity in Vivo

Haloperidol-induced Hypolocomotion Model

It has previously been demonstrated that adenosine antagonists, such as theophylline, can reverse the behavioural depressant effects of dopamine antagonists, such as haloperidol, in rodents (Mandhane S. N. et al., Adenosine A$_2$ receptors modulate haloperidol-induced catalepsy in rats. *Eur. J. Pharmacol.* 1997, 328, 135–141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25–30 g) obtained from TUCK, UK, are used for all experiments. Animals are housed in groups of 8 [cage size–40 (width)×40 (length)×20 (height)cm] under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Liquid injectable haloperidol (1 ml Serenance ampoules from Baker Norton, Harlow, Essex, each containing haloperidol BP 5 mg, batch # P424) are diluted to a final concentration of 0.02 mg/ml using saline. Test compounds are typically prepared as aqueous suspensions in 8% Tween. All compounds are administered intraperitoneally in a volume of 10 ml/kg.

Procedure 1.5 hours before testing, mice are administered 0.2 mg/kg haloperidol, a dose that reduces baseline locomotor activity by at least 50%. Test substances are typically administered 5–60 minutes prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 3×6 array of photocells linked to a computer, which tabulates beam breaks. Mice are left undisturbed to explore for 1 hour, and the number of beams breaks made during this period serves as a record of locomotor activity which is compared with data for control animals for statistically significant differences.

6-OHDA Model

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal dopamine is lost (ca 80–85%) before symptoms are observed. The loss of striatal dopamine results in abnormal activity of the basal ganglia, a series of nuclei which regulate smooth and well co-ordinated movement (Blandini F. et al., Glutamate and Parkinson's Disease. *Mol. Neurobiol.* 1996, 12, 73–94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersenstive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Animals

Male Sprague-Dawley rats, obtained from Charles River, are used for all experiments. Animals are housed in groups of 5 under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Ascorbic acid, desipramine, 6-OHDA and apomorphine (Sigma-Aldrich, Poole, UK). 6-OHDA is freshly prepared as a solution in 0.2% ascorbate at a concentration of 4 mg/mL prior to surgery. Desipramine is dissolved in warm saline, and administered in a volume of 1 ml/kg. Apomorphine is dissolved in 0.02% ascorbate and administered in a volume of 2 mL/kg. Test compounds are suspended in 8% Tween and injected in a volume of 2 mL/kg.

Surgery 15 minutes prior to surgery, animals are given an intraperitoneal injection of the noradrenergic uptake inhibitor desipramine (25 mg/kg) to prevent damage to non-dopamine neurones. Animals are then placed in an anaesthetic chamber and anaesthetised using a mixture of oxygen and isoflurane. Once unconscious, the animals are transferred to a stereotaxic frame, where anaesthesia is maintained through a mask. The top of the animal's head is shaved and sterilised using an iodine solution. Once dry, a 2 cm long incision is made along the midline of the scalp and the skin retracted and clipped back to expose the skull. A small hole is then drilled through the skill above the injection site. In order to lesion the nigrostriatal pathway, the injection cannula is slowly lowered to position above the right medial forebrain bundle at −3.2 mm anterior posterior, −1.5 mm medial lateral from bregma, and to a depth of 7.2 mm below the duramater. 2 minutes after lowing the cannula, 2 μL of 6-OHDA is infused at a rate of 0.5 μL/min over 4 minutes, yeilding a final dose of 8 μg. The cannula is then left in place for a further 5 minutes to facilitate diffusion before being slowly withdrawn. The skin is then sutured shut using Ethicon W501 Mersilk, and the animal removed from the strereotaxic frame and returned to its homecage. The rats are allowed 2 weeks to recover from surgery before behavioural testing.

Apparatus

Rotational behaviour is measured using an eight station rotameter system provided by Med Associates, San Diego, USA. Each station is comprised of a stainless steel bowl (45 cm diameter×15 cm high) enclosed in a transparent Plexiglas cover running around the edge of the bowl, and extending to a height of 29 cm. To assess rotation, rats are placed in cloth jacket attached to a spring tether connected to optical rotameter positioned above the bowl, which assesses movement to the left or right either as partial (45°) or full (360°) rotations. All eight stations are interfaced to a computer that tabulated data.

Procedure

To reduce stress during drug testing, rats are initially habituated to the apparatus for 15 minutes on four consecutive days. On the test day, rats are given an intraperitoneal injection of test compound 30 minutes prior to testing. Immediately prior to testing, animals are given a subcutaneous injection of a subthreshold dose of apomorphine, then placed in the harness and the number of rotations recorded for one hour. The total number of full contralatral rotations during the hour test period serves as an index of antiparlinsonian drug efficacy.

The invention claimed is:

1. A compound of formula (I):

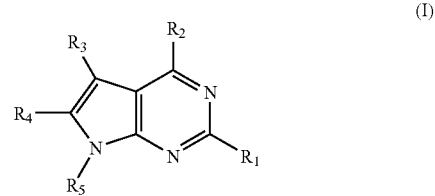

wherein
- $R_1$ is selected from the group consisting of alkyl, alkoxy, aryloxy, alkylthio, arylthio, aryl, halogen, CN, $NR_7R_8$, $NR_6COR_7$, $NR_6CONR_7R_8$, $NR_6CO_2R_9$, and $NR_6SO_2R_9$;
- $R_2$ is a heteroaryl, attached via an unsaturated ring carbon of said heteroaryl group, other than pyrrolopyrimidine;
- $R_3$ and $R_4$ are independently selected from the group consisting of H, alkyl, halogen, alkoxy, alkylthio, CN, and $NR_7R_8$;
- $R_5$ is selected from the group consisting of H, acyclic alkyl, $COR_6$, $CONR_7R_8$, $CONR_6NR_7R_8$, $CO_2R_9$, and $SO_2R_9$;
- $R_6$, $R_7$, and $R_8$ are independently selected from the group consisting of H, alkyl, and aryl, or where $R_7$ and $R_8$ are in an $NR_7R_8$ group $R_7$ and $R_8$ may be linked to form a heterocyclic group, or where $R_6$, $R_7$, and $R_8$ are in a ($CONR_6NR_7R_8$) group, $R_6$ and $R_7$ may be linked to form a heterocyclic group; and
- $R_9$ is selected from alkyl and aryl, or a pharmaceutically acceptable salt thereof.

2. The compound of claim 1, wherein $R_1$ is selected from the group consisting of alkyl, alkoxy, thioalkyl, $NR_7R_8$, $NR_6COR_7$, $NR_6CONR_7R_8$, $NR_6CO_2R_9$, and $NR_6SO_2R_9$.

3. The compound of claim 1, wherein $R_1$ is selected from the group consisting of $NR_7R_8$, $NR_6COR_7NR_6CONR_7R_8$, $NR_6CO_2R_9$, and $NR_6SO_2R_9$.

4. The compound of claim 1, wherein $R_1$ is $NR_7R_8$.

5. The compound of claim 1, wherein $R_1$ is $NH_2$.

6. The compound of claim 1, wherein $R_1$ is selected from the group consisting of $NR_6COR_7$, $NR_6CONR_7R_8$, $NR_6CO_2R_9$ and $NR_6SO_2R_9$, and $R_6$ is H or alkyl.

7. The compound of claim 1, wherein $R_1$ is selected from the group consisting of $NR_6COR_7$, $NR_6CONR_7R_8$, $NR_6CO_2R_9$ and $NR_6SO_2R_9$, and $R_6$ is H.

8. The compound of claim 1, wherein $R_1$ is selected from the group consisting of haloalkyl and arylalkyl.

9. The compound of claim 1, wherein $R_2$ is a 5- or 6-membered monocyclic heteroaryl group.

10. The compound of claim 1, wherein $R_2$ is unsubstituted in at least one ortho position.

11. The compound of claim 1, wherein $R_2$ is unsubstituted at both ortho positions.

12. The compound of claim 1, wherein $R_2$ is a heteroaryl group which is attached to the pyrimidine ring of formula (I) such that a heteroatom is adjacent to said unsaturated carbon atom attached to the pyrimidine ring.

13. The compound of claim 1, wherein $R_2$ is an N, O or S-containing heteroaryl group.

14. The compound of claim 1, wherein $R_2$ is selected from the group consisting of furyl, thienyl, pyridyl, pyrazolyl and thiazolyl.

15. The compound of claim 1, wherein $R_2$ is selected from the group consisting of 2-furyl, 2-thienyl, 2-thiazolyl, 3-pyrazolyl, and 2-pyridyl.

16. The compound of claim 1, wherein $R_3$ is hydrogen.

17. The compound of claim 1, wherein $R_4$ is hydrogen.

18. The compound of claim 1, wherein $R_5$ is selected from the group consisting of H and substituted acyclic alkyl.

19. The compound of claim 18, wherein $R_5$ is acyclic alkyl substituted by a substituent selected from the group consisting of aryl, cycloalkyl, non-aromatic heterocyclyl, $CO_2R_6$, $CONR_7R_8$, $CONR_6NR_7R_8$, and $C(=NR_6)NR_7R_8$.

20. The compound of claim 19, wherein $R_5$ is acyclic alkyl substituted by aryl or $CONR_7R_8$.

21. The compound of claim 20, wherein $R_5$ is methyl substituted by aryl or $CONR_7R_8$.

22. The compound of claim 1, wherein $R_5$ is $(CR_{10}R_{11})_n R_{12}$, wherein:
n is 1 to 6,
$R_{10}$ and $R_{11}$ are independently selected from H, alkyl, and aryl, and
$R_{12}$ is selected from the group consisting of substituted and unsubstituted aryl, cycloalkyl, non-aromatic heterocyclic, $CO_2R_6$, $CONR_7R_8$, $CONR_6NR_7R_8$, and $C(=NR_6)NR_7R_8$.

23. The compound of claim 22, wherein n is 1.

24. The compound of claim 22, wherein $R_{10}$ and $R_{11}$ are independently selected from H and alkyl.

25. The compound of claim 22, wherein $R_{12}$ is selected from aryl and $CONR_7R_8$.

26. The compound of claim 22, wherein $R_{12}$ is selected from mono-, di- or tri-substituted aryl groups represented by the formula $Ar(R_{13})_a(R_{14})_b(R_{15})_c$ wherein:
Ar is an aryl group;
$R_{13}R_{14}$ and $R_{15}$ are substituent group(s), the same or different; and a, b and c are 0 or 1 such that $a+b+c \geq 1$.

27. The compound of claim 25, wherein said aryl group is selected from the group consisting of phenyl, thienyl, furyl, indolyl and pyridyl.

28. The compound of claim 25, wherein $R_{13}$, $R_{14}$ and $R_{15}$ are independently selected from the group consisting of $NR_7R_8$, alkyl, alkoxy, halogen, $NO_2$, CN, hydroxy, NHOH, CHO, $CONR_7R_8$, $CO_2R_7$, $NR_6COR_7$, $NR_6CO_2R_9$, $NR_6SO_2R_9$, $OCO_2R_9$, and aryl.

29. The compound of claim 28, wherein $R_{13}$, $R_{14}$ and $R_{15}$ are independently selected from the group consisting of $NR_7R_8$, alkyl, and halogen.

30. The compound of claim 28, wherein $R_{13}$, $R_{14}$ and $R_{15}$ are independently selected from a substituted alkyl, wherein said substituent is selected from the group consisting of alkoxyalkyl, hydroxyalkyl, aminoalkyl, and haloalkyl.

31. The compound of claim 29, wherein $R_{13}$, $R_{14}$ and $R_{15}$ are independently selected from the group consisting of $NH_2$, unsubstituted alkyl, and fluoro.

32. The compound of claim 22, wherein $R_{12}$ is $CONR_7R_8$, $R_7$ is H, and $R_8$ is selected from the group consisting of H, unsubstituted alkyl, and arylalkyl.

33. The compound of claim 1, wherein $R_5$ is $CONR_7R_8$, $R_7$ is H, and $R_8$ is arylalkyl.

34. The compound of claim 33, wherein $R_8$ is arylmethyl.

35. The compound of claim 1, wherein $R_6$ to $R_{11}$ are independently selected from lower alkyl.

36. The compound of claim 1, wherein $R_1$ is $NH_2$, $R_2$ is 2-furyl, $R_3$ and $R_4$ are H, and $R_5$ is arylmethyl.

37. The compound of claim 1, wherein the compound of formula (I) is 7-(2-fluorobenzyl)-4-(2-furyl)-7H-pyrrolo[2,3-d]pyrimidine-2-amine.

* * * * *